United States Patent
Kapoor et al.

(10) Patent No.: US 10,980,509 B2
(45) Date of Patent: Apr. 20, 2021

(54) DEFORMABLE REGISTRATION OF PREOPERATIVE VOLUMES AND INTRAOPERATIVE ULTRASOUND IMAGES FROM A TRACKED TRANSDUCER

(71) Applicant: Siemens Medical Solutions USA, Inc., Malvern, PA (US)

(72) Inventors: Ankur Kapoor, Plainsboro, NJ (US); Thomas Pheiffer, Langhorne, PA (US); Jin-hyeong Park, Princeton, NJ (US); Ali Kamen, Skillman, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 578 days.

(21) Appl. No.: 15/592,482

(22) Filed: May 11, 2017

(65) Prior Publication Data

US 2018/0330497 A1   Nov. 15, 2018

(51) Int. Cl.
*A61B 8/00* (2006.01)
*A61B 5/107* (2006.01)
(Continued)

(52) U.S. Cl.
CPC .......... *A61B 8/4245* (2013.01); *A61B 5/1073* (2013.01); *A61B 5/1075* (2013.01);
(Continued)

(58) Field of Classification Search
CPC ... A61B 8/4245; A61B 5/1075; A61B 8/5261; A61B 5/1073; A61B 8/483; A61B 8/466; A61B 5/0035; A61B 2034/2055; A61B 2034/2048; A61B 34/20; A61B 5/055; A61B 8/488; A61B 90/37; A61B 2090/378; A61B 34/10; A61B 2034/105; A61B 2034/107; A61B 2090/364; A61B 2034/2051–2057; A61B 2034/2068–2074; A61B 8/4444–4477; A61B 8/4483–4494; A61B 8/46–466; G06T 7/344; G06T 2207/30056; G06T 2207/10132; G06T 2207/10088; G06T 3/0068; G06T 5/50; G06T 7/30
(Continued)

(56) References Cited

U.S. PATENT DOCUMENTS 4,576,047 A * 3/1986 Lauer .................. G01P 5/245
73/597
4,644,483 A * 2/1987 Lauer .................. G01P 5/245
367/123

(Continued)

OTHER PUBLICATIONS

Burcher ["Deformation Correction in Ultrasound Images using Contact Force Measurements", IEEE 2001], (Year: 2001).*
(Continued)

*Primary Examiner* — Oommen Jacob (57) ABSTRACT

Methods and systems are provided for registration of preoperative images to ultrasound images. The preoperative images are segmented using a shape model. An ultrasound procedure is performed to acquire the ultrasound images. The path of an ultrasound transducer used in the ultrasound procedure is tracked. The path is used to deform the segmented preoperative images, providing an alignment. The ultrasound images are registered to the preoperative images using the alignment.

14 Claims, 6 Drawing Sheets

(51) Int. Cl.
*A61B 8/08* (2006.01)
*G06T 7/33* (2017.01)
*A61B 34/20* (2016.01)
*A61B 5/055* (2006.01)
*A61B 5/00* (2006.01)
*A61B 34/10* (2016.01)
*A61B 90/00* (2016.01)

(52) U.S. Cl.
CPC .............. *A61B 8/466* (2013.01); *A61B 8/483* (2013.01); *A61B 8/5261* (2013.01); *G06T 7/344* (2017.01); *A61B 5/0035* (2013.01); *A61B 5/055* (2013.01); *A61B 34/20* (2016.02); *A61B 2034/105* (2016.02); *A61B 2034/2048* (2016.02); *A61B 2034/2051* (2016.02); *A61B 2034/2055* (2016.02); *A61B 2090/378* (2016.02); *G06T 2207/10088* (2013.01); *G06T 2207/10132* (2013.01); *G06T 2207/30056* (2013.01)

(58) Field of Classification Search
USPC ........................................ 600/411, 407, 408
See application file for complete search history.

(56) References Cited

U.S. PATENT DOCUMENTS

| | | | | |
|---|---|---|---|---|
| 5,817,022 | A * | 10/1998 | Vesely | A61B 34/20 600/443 |
| 5,868,673 | A * | 2/1999 | Vesely | A61B 8/4245 600/407 |
| 5,941,825 | A * | 8/1999 | Lang | A61B 5/4872 600/449 |
| 6,019,725 | A * | 2/2000 | Vesely | A61B 8/0841 128/916 |
| 6,490,473 | B1 * | 12/2002 | Katznelson | A61B 5/055 600/410 |
| 7,356,172 | B2 * | 4/2008 | Fan | G06T 7/246 382/107 |
| 7,714,855 | B2 * | 5/2010 | Brabec | G06T 15/08 345/418 |
| 8,165,659 | B2 * | 4/2012 | Sheffer | A61B 34/20 600/427 |
| 2002/0035321 | A1 * | 3/2002 | Bucholz | A61B 5/0064 600/407 |
| 2004/0019274 | A1 * | 1/2004 | Galloway, Jr. | A61B 34/20 600/425 |
| 2005/0085718 | A1 * | 4/2005 | Shahidi | A61B 8/0833 600/424 |
| 2005/0251029 | A1 * | 11/2005 | Khamene | A61B 8/4245 600/427 |
| 2006/0237652 | A1 * | 10/2006 | Kimchy | G06T 5/50 250/363.02 |
| 2006/0253031 | A1 * | 11/2006 | Altmann | G06T 7/38 600/466 |
| 2007/0270680 | A1 * | 11/2007 | Sheffer | A61B 90/36 600/407 |
| 2007/0276234 | A1 * | 11/2007 | Shahidi | A61B 8/0833 600/437 |
| 2008/0247622 | A1 * | 10/2008 | Aylward | A61B 90/36 382/131 |
| 2011/0081063 | A1 * | 4/2011 | Leroy | A61B 8/0841 382/131 |
| 2011/0082363 | A1 * | 4/2011 | Xu | A61B 34/20 600/411 |
| 2012/0140998 | A1 * | 6/2012 | Zhu | G06T 5/006 382/128 |
| 2012/0155734 | A1 * | 6/2012 | Barratt | G06T 7/35 382/131 |
| 2013/0090554 | A1 * | 4/2013 | Zvuloni | A61B 10/0241 600/424 |
| 2013/0324841 | A1 * | 12/2013 | Kamen | A61B 8/0841 600/424 |
| 2015/0327841 | A1 * | 11/2015 | Banjanin | A61B 8/5276 600/443 |
| 2016/0007970 | A1 * | 1/2016 | Dufour | A61B 8/58 600/437 |
| 2016/0350503 | A1 * | 12/2016 | Jun | A61B 8/54 |
| 2017/0325785 | A1 * | 11/2017 | Lieblich | A61B 8/4483 |
| 2017/0360578 | A1 * | 12/2017 | Shin | B33Y 30/00 |
| 2018/0330497 | A1 * | 11/2018 | Kapoor | A61B 8/4245 |

OTHER PUBLICATIONS

Goskel ["Image-Based Variational Meshing" IEEE Transactions on Medical Imaging, vol. 30, No. 1, Jan. 2011] (Year: 2011).*
Burger ["Real-Time GPU-Based Ultrasound Simulation Using Deformable Mesh Models" IEEE Transactions on Medical Imaging, vol. 32, No. 3, Mar. 2013 (Year: 2013).*
Goksel ["B-Mode Ultrasound Image Simulation in Deformable 3-D Medium" IEEE Transactions on Medical Imaging, vol. 28, No. 11, Nov. 2009] (Year: 2009).*
Barbara ["Model-Based Compensation of Tissue Deformation During Data Acquisition for Interpolate Ultrasound Simulation" IEEE 2016] (Year: 2016).*
Yeung ["Feature-Adaptive Motion Tracking of Ultrasound Image Sequences Using a Deformable Mesh" IEEE Transactions on Medical Imaging, vol. 17, No. 6, Dec. 1998] (Year: 1998).*
Marami ["Dynamic tracking of a deformable tissue based on 3D-2D MR-US image registration" SPIE Medical Imaging, 2014] (Year: 2014).*
A. Myronenko and Xubo Song, "Point Set Registration: Coherent Point Drift," IEEE Trans. Pattern Anal. Mach. Intell., vol. 32, No. 12, pp. 2262-2275, Dec. 2010.
B. van Ginneken, A. F. Frangi, J. J. Staal, B. M. ter Haar Romeny, and M. A. Viergever, "Active shape model segmentation with optimal features," IEEE Trans. Med. Imaging, vol. 21, No. 8, pp. 924-933, Aug. 2002.
J. H. Park, S. K. Zhou, C. Simopoulos, J. Otsuki, and D. Comaniciu, "Automatic Cardiac View Classification of Echocardiogram," 2007.
P. J. Besl and H. D. McKay, "A method for registration of 3-D shapes," IEEE Trans. Pattern Anal. Mach. Intell., vol. 14, No. 2, pp. 239-256, Feb. 1992.
S. Khallaghi, C. A. Sanchez, A. Rasoulian, S. Nouranian, C. Romagnoli, H. Abdi, S. D. Chang, P. C. Black, L. Goldenberg, W. J. Morris, I. Spadinger, A. Fenster, A. Ward, S. Fels, and P. Abolmaesumi,"Statistical Biomechanical Surface Registration: Application to MR-TRUS Fusion for Prostate Interventions," IEEE Trans. Med. Imaging, vol. 34, No. 12, pp. 2535-2549, Dec. 2015.
T. F. Cootes, G. J. Edwards, and C. J. Taylor, "Active appearance models," IEEE Trans. Pattern Anal. Mach. Intell., vol. 23, No. 6, pp. 681-685, Jun. 2001.

* cited by examiner

DEFORMABLE REGISTRATION OF PREOPERATIVE VOLUMES AND INTRAOPERATIVE ULTRASOUND IMAGES FROM A TRACKED TRANSDUCER

BACKGROUND

The present embodiments relate to registration of intra-operative ultrasound images to preoperative images.

In order for preoperative images to be effectively used to supplement ultrasound guidance, an image registration procedure combines the preoperative data and ultrasound images into a common coordinate space. Image registration is the process of overlaying or fusing together two or more images from the same scene taken at different times, from different viewpoints, and/or different sensors.

In clinical practice, image registration may be accomplished manually by a user after viewing both images. Manual registration may be quick, but very inaccurate. Additionally, there are a number of techniques to perform the registration automatically using computational algorithms. For example, feature detection may identify edges, regions, boundaries etc. in both sets of images. Feature matching may determine a correspondence of the detected features in both images. A mapping function may align the two images together. The images may be overlaid in a single view.

Feature detection, feature mapping, and mapping functions work well with static scenes. For example, in landscape planning or mapping, features may not move and thus may be matched with a high level of accuracy. However, for medical procedures, feature mapping may be insufficient to accurately align structures due to soft tissue deformation or movement that occurs during the imaging process.

BRIEF SUMMARY

By way of introduction, the preferred embodiments described below include methods, and systems for registration of preoperative images to ultrasound images. The preoperative images are segmented using a shape model. An ultrasound procedure is performed to acquire the ultrasound images. The path of an ultrasound probe used in the ultrasound procedure is tracked. The path is used to deform the segmented preoperative images, providing a partial alignment. The ultrasound images are registered to the preoperative images using the partial alignment.

In a first aspect, a method is provided for registration of a preoperative volume and ultrasound data. A geometry of an organ is generated from the preoperative volume. The geometry comprises at least one or more anatomical landmarks. A path of an ultrasound transducer over the one or more anatomical landmarks is tracked during a procedure to acquire the ultrasound data. The geometry is deformed as a function of the path. The preoperative volume is registered with the ultrasound data using the deformed geometry.

In a second aspect, a method is provided for registration of a preoperative volume and ultrasound data. The preoperative volume is segmented using a shape model. A sweep of a transducer over a body of a patient is tracked during an ultrasound procedure that acquires the ultrasound data. The segmented preoperative volume is deformed with a biomechanical model of organ deformation using the tracked sweep as a boundary condition. The ultrasound data is segmented using the deformed segmented preoperative volume as an initial shape representation. An alignment is generated between the segmented preoperative volume and the segmented ultrasound data.

In a third aspect, a system is provided for registration of a preoperative volume and an ultrasound volume. The system includes a medical imaging system, an ultrasound transducer, a tracker, and a processor. The medical imaging system is configured to acquire the preoperative volume. The ultrasound transducer is configured to acquire the ultrasound volume. The tracker is configured to track the ultrasound transducer. The processor is configured to generate a segmented volume of the preoperative volume. The processor is further configured to deform the segmented model using the tracked path of the ultrasound transducer and register the ultrasound volume with the deformed segmented model.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION

Registration of intra-operative ultrasound images to pre-operative images and bringing the modalities and tools into a common frame of reference is an often-encountered problem in image guided therapy. Embodiments herein provide an accurate and efficient registration of preoperative images with intra-operative images by computing a deformation that occurs during an ultrasound procedure. A user sweeps an ultrasound transducer over one or more pre-identified structures. The ultrasound transducer is tracked during the sweep. The tracked sweep path is used to perform an alignment between a segmented shape model from the preoperative images and the ultrasound images acquired during the procedure. The alignment is used to register the preoperative images to the ultrasound images.

Registration of images entails determining a correspondence between points in two different image and adjusting one or both of the images so that the two images may be used with a single coordinate system. One known method of registration uses feature detection and feature mapping between two images taken at separate times, from different viewpoints, and/or using different sensors. When used in a medical setting, this method of feature detection and feature mapping may have drawbacks.

Initially in feature detection the kind or type of features are determined. Features may be distinct objects that appear in each of the images to be registered. The detected features in the images may have enough common elements, even in situations when the images do not cover exactly the same scene or when there are object occlusions or other unexpected changes. The detection methods may have good localization accuracy and may not be sensitive to the any image degradation. For a perfect scenario, a feature mapping algorithm may be able to detect each and every one of the same features in all images of the scene regardless of any image deformation or changes. In many scenarios, the one or more features may not be detected in all of the images.

Figure 1A:
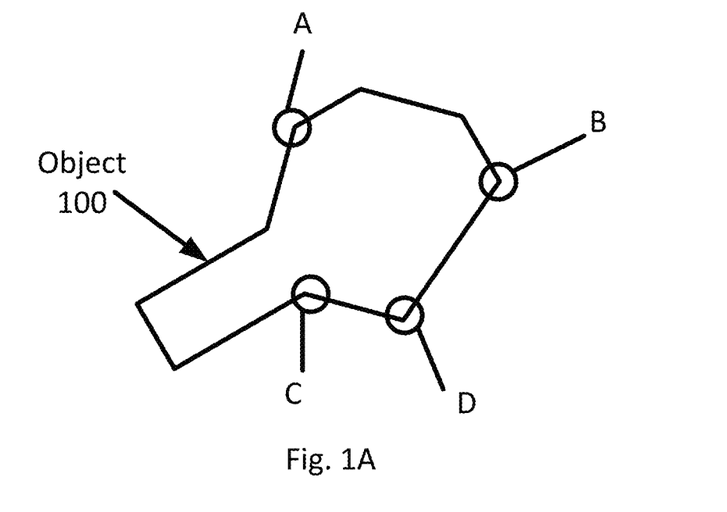
FIGS. 1A and 1B depict examples of feature identification and mapping.

FIG. 1A depicts feature detecting for an image. The object 100 in FIG. 1A includes nine vertices, four of which are labeled A, B, C, and D. The four labeled vertices may be considered a set of features of the object 100. Each of A, B, C, and D may be easily recognizable in multiple different views of the object 100, such as by applying a machine-learnt detector, gradient process, boundary detector, segmentation, or other image process.

After the set of features is selected, the features or points from each image are mapped to one another. Each feature or point from a first image may have a corresponding feature or point in a second image. The feature correspondences may exist for each feature or point. Due to movement, image degradation, deformation, etc. each feature of point may not have a corresponding feature or point in the second image. After the feature correspondence has been established the mapping function is constructed. The mapping function may transform the first image (or visa versa) to overlay the first image over the second image. The mapping function may employ a simple distance algorithm that provides that corresponding point points may be as close as possible after the image transformation.

Figure 1B:
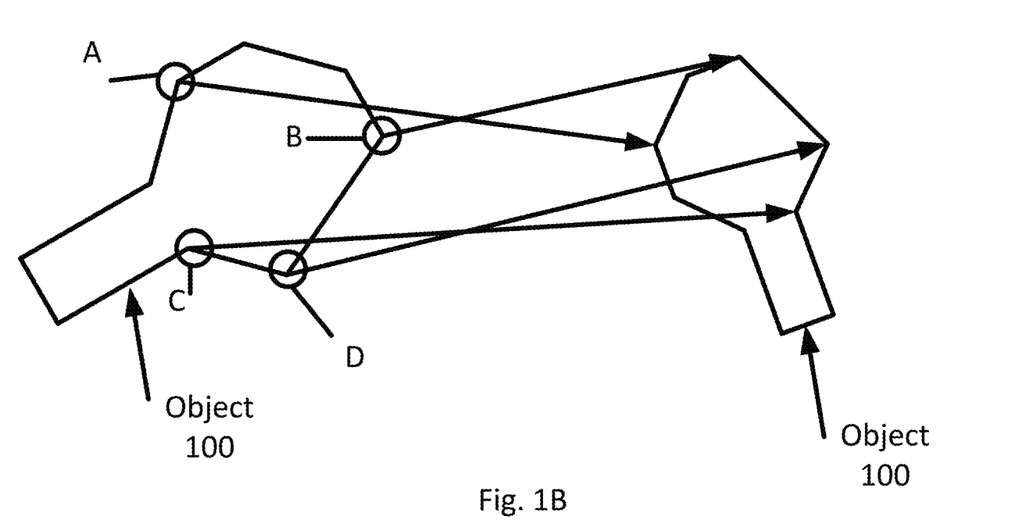

Feature 1B depicts feature mapping for two images of the object 100 of FIG. 1A. The image on the left is a duplicate of the figure of FIG. 1A. The image on the right is a view of the object 100 taken from a different angle. Directly overlaid over each other, the two images would not line up. However, as the two images depict the same object 100, feature correspondences may be identified. The feature set of A, B, C, and D is identified in the second image. Different methods may be used to identify the features. For example, in facial recognition, a corner of an eye may be used as a feature. The corner of an eye may be easily recognizable by a user or automatically by an image processor using methods such as edge detection. Once the features are mapped between the images, the images may be registered. The registration may further include deforming or altering one of the images so that the images may exist in a single coordinate space. In the example of FIG. 1B, the second image may be rotated and expanded so that when overlaid, the two images line up. The matrix representing the rotation and expansion is a transformation of the second image into the coordinate space of the first image. Affine or rigid transformations may be used.

For medical images, for example ultrasound images, issues may arise during a feature detection and mapping process. The use of an ultrasound probe may deform the organ or tissues during the application of the probe. As a result, correspondence between features in the preoperative images and features in the ultrasound images may be difficult to achieve. Features may be detected in both images, but the mapping function may fail to produce an accurate registration as certain points may have moved differently than other points due to the probe deformation. Point set registration, also known as point matching, is the process of finding a spatial transformation that aligns the two point sets of the images.

A point registration problem may be formulated as minimization of the distance between two point sets, with the second point set transformed by the registration transformation parameters and a permutation matrix P, that defines the matching between the two points sets. Elements of matrix P are either 0 or 1, making the problem NP-hard. Various local methods, such as coherent point drift (CPD) or iterative closest point (ICP), use distance criteria to iteratively determine P followed by the registration transformation parameters. CPD, ICP, and other methods may fail to achieve a good registration due to the unpredictability of the deformation due to the probe. Without additional information, the registration may be lacking.

Embodiments herein provide the additional information as correspondences between geometry from the preoperative images and geometry from a trajectory of a three-dimensional sweep by an ultrasound probe. The correspondences are used to force a model created from the preoperative image to match the ultrasound image.

Figure 2:
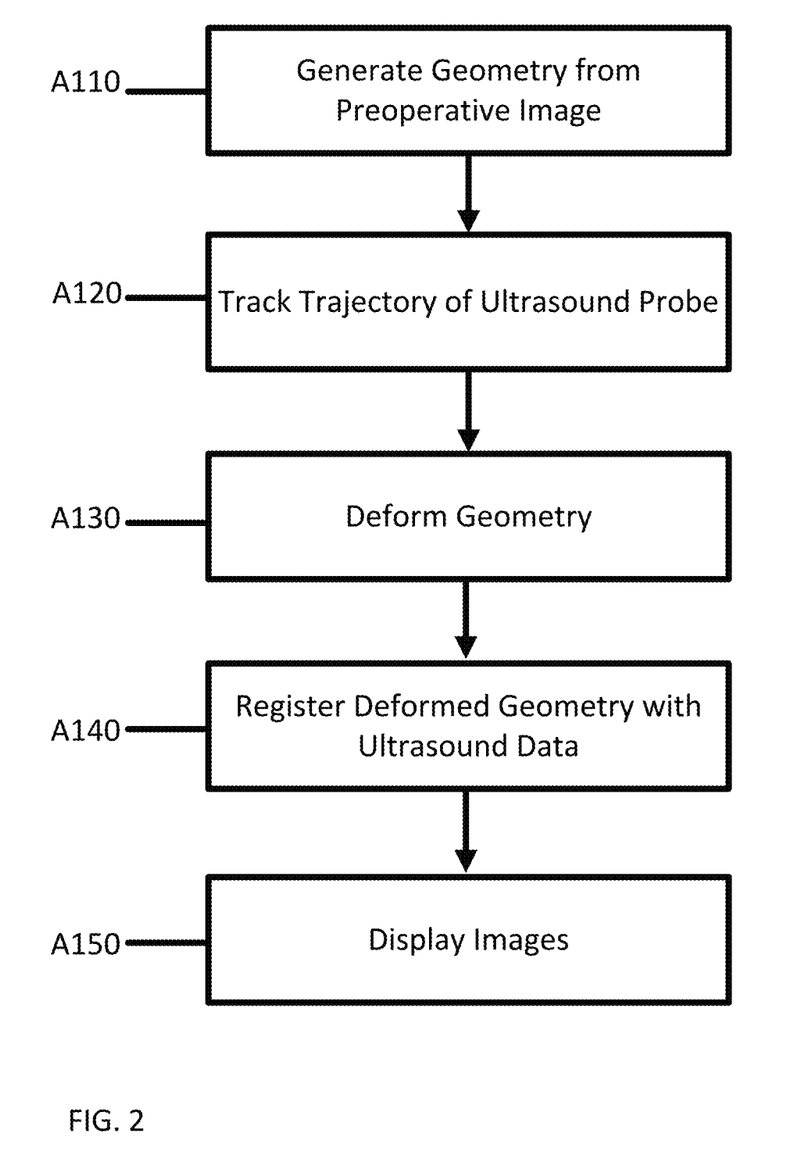
FIG. 2 depicts a flow chart of one embodiment of a method for registration of intra-operative ultrasound images to preoperative images.

FIG. 2 depicts a flow chart of one embodiment of a method for registering preoperative images with ultrasound images. The method relates to automatically determining the deformation due to an ultrasound procedure and using the determined deformation to register an ultrasound image with a previously captured image or volume.

Figure 6:
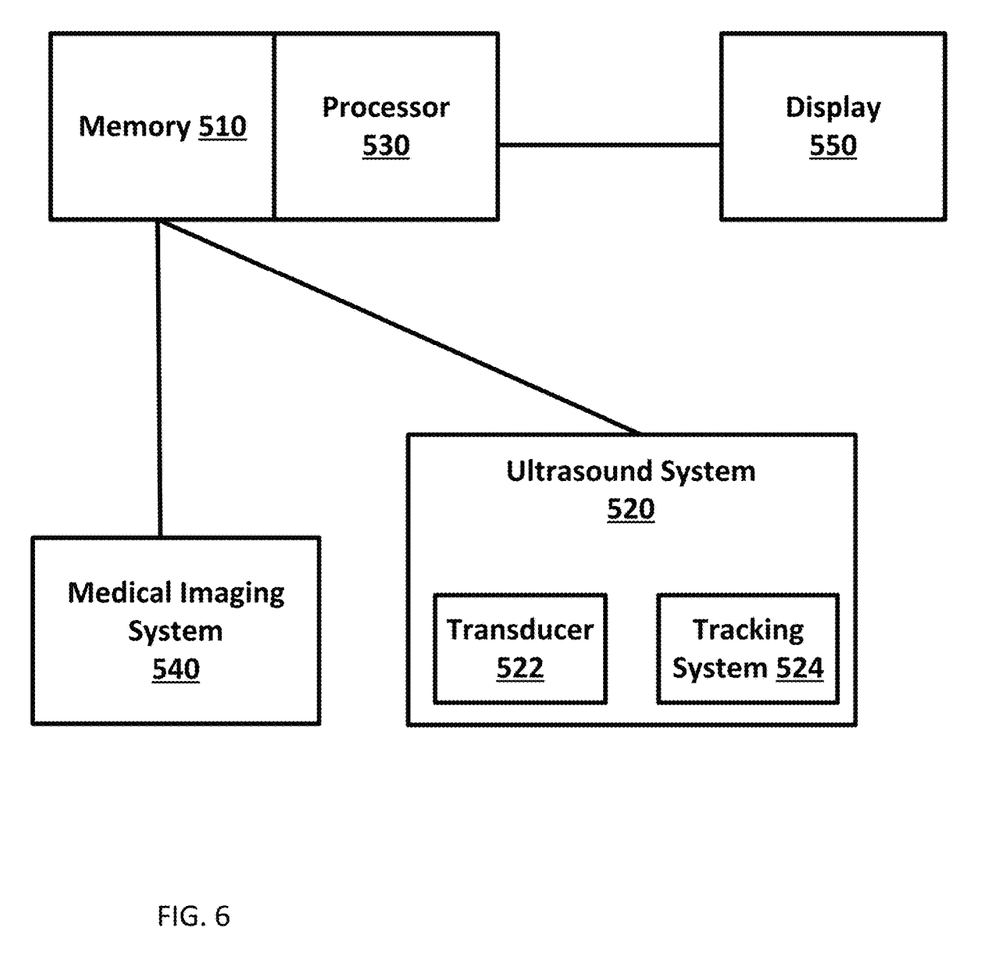
FIG. 6 depicts a block diagram of one embodiment of a medical system for registration of intra-operative ultrasound images to preoperative images.

The medical system of FIG. 6 or other medical system implements the acts. The system may be a medical imaging system, a hospital workstation, a medical server, or other secure medical data processing system. The medical system may or may not include a memory or database, such as patient medical record database and/or picture archiving and communications system (PACS).

The acts of FIG. 2 are performed in the order shown (numerical or top to bottom) or other orders. For example, acts A130 and A140 occur simultaneously or in any order. Additional, different, or fewer acts may be provided. Example additional acts include selecting landmarks or displaying the registered image and volume together.

At act A110, a geometry of an organ is generated from a preoperative image data or volume. Image data may be scalar values that may be used to generate an image or may be actual display values for display of the image.

The preoperative image data may represent an internal structure in a patient. In the examples below, medical imaging or scanner data is used. In other embodiments, other types of data are used. A medical scanner may provide the image data, such as a medical dataset representing a 2D slice or 3D region of the patient. Any type of image data may be obtained, such as computed tomography, magnetic resonance, positron emission tomography, single photon emission computed tomography, ultrasound, or another scan modality. The scan data may represent one or more objects, for example, the internal organs of a patient.

The preoperative image data may be obtained prior to the ultrasound images in Act A130. The preoperative image data may be obtained simultaneously or concurrently as the ultrasound images in Act A130. The preoperative image data may be stored in a memory or acquired from other sources, for example, a PACS.

The preoperative image data may be segmented using a shape model technique (e.g. an active shape technique). The shape model provides that indices are ordered consistently, and any labeling of an average shape is propagated to the segmented image. Alternative methods, such as appearance models, active contours, statistical shape models, or templates, may be used for segmentation of the preoperative image.

Shape model-based methods make use of a prior model of what is expected in the image, and attempt to find the best match of the model to the data in a new image data. Landmark points, such as surface mesh indices or labels, are identified. The landmark points are points that may be easy to identify and mark in each image. The shape model uses the landmark points to generate one or more expected images shapes for the model. For example, machine learning is used to generate the shape model. The model may further be annotated or adjusted by a user or expert. In other embodiments, an expert created shape model or a shape model based on a clinical study is used.

A shape model may be provided of the organ or an object in the image data. The shape model may be derived or trained from previous scans of the patient or other patients. An object is described by points, referred to as landmark points. The landmark points may be determined in a set of training images. From the landmark points, a point distribution model is constructed. Principal component analysis (PCA) may be applied to the point in the point distribution model to fit the model. The model, e.g. the average shape of the organ, may be stored in a memory or acquired from other sources such as medical record database or PACS.

The shape model may include labels for landmark or key points. A landmark may be, for example, an anatomical landmark. Anatomical landmarks may include points on or in an anatomical structure, for example, an organ, that may be present in similar organs from different patients. For example, general anatomy divides a liver into two portions, right and left lobes. Anatomical landmarks or regions for a liver include the division between the lobes, e.g. the falciform ligament. Further, a line may be drawn running from the left of the vena cava and all the way forward to divide the liver and gallbladder into two halves. Other anatomical landmarks exist, such as the ligamentum venosum and the round ligament of the liver (ligamentum teres), that further divide the left side of the liver in two sections. The porta hepatis, also known as the transverse fissure of the liver, divides this left portion into four segments. Each of these anatomical landmarks exist in livers from different patients and as such may be used to define an average shape model for a specific type of organ. The average shape model for an organ may include a set of landmark points. Connecting the points may provide a wire frame model of the organ.

The average shape model may be used to identify the organ in the preoperative images by using one or more fitting functions. For preoperative image data, specific landmarks may be selected automatically or by a user. Preoperative image data may not contain each of the landmarks for an organ. For example, different views of an organ may block out landmarks on the opposite site of the organ. As such, only the landmarks that are visible in the preoperative image data may be used.

Using the shape model and the landmarks, the preoperative image data may be segmented. Image segmentation may be used to locate boundaries or edges in the image data. Image segmentation may assign a value or labels to pixels in an image so that groups of pixels may share similar characteristics. Using a shape model, segmentation includes fitting the preoperative image to the average shape model. The shape model may be fit with the preoperative image by identifying the landmarks in the preoperative image and matching the points to the landmarks in the shape model. An iterative approach may be used to improve the fit to the preoperative image.

Figure 3:
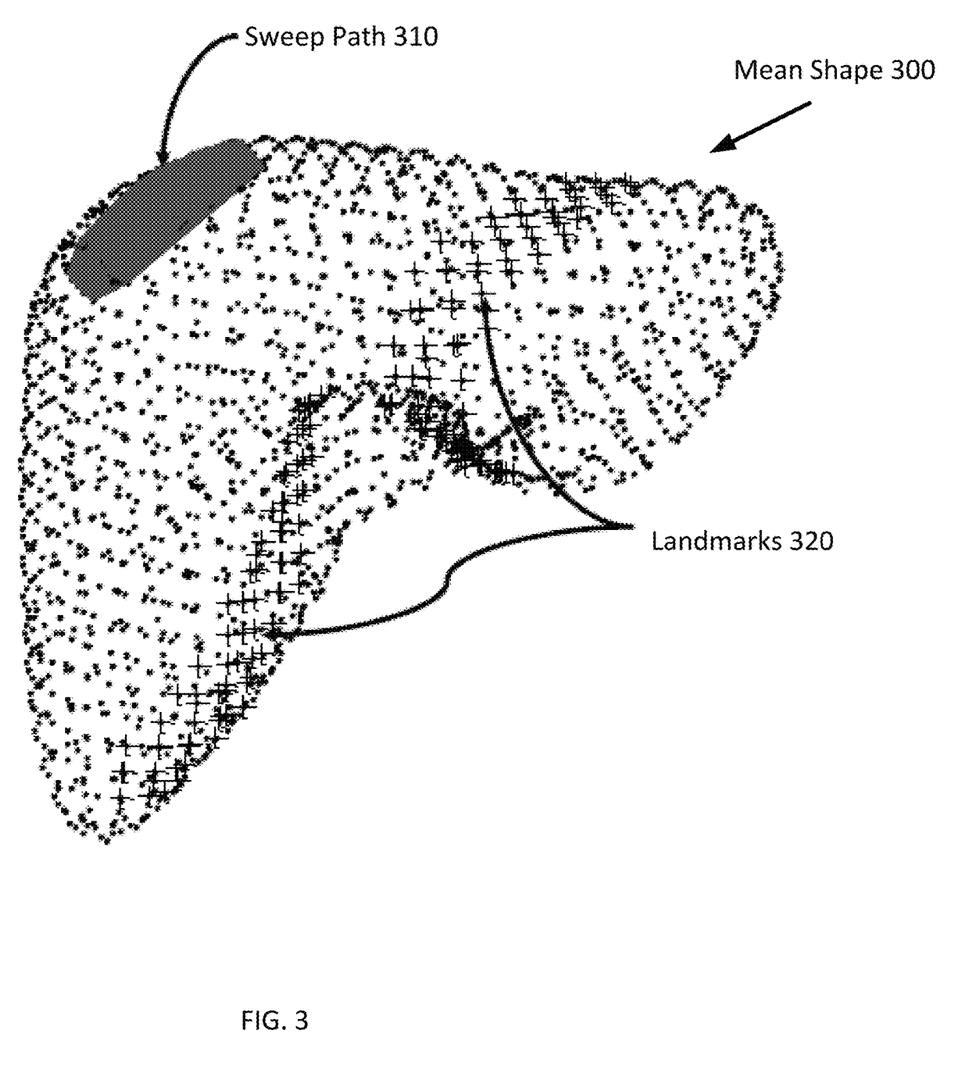
FIG. 3 depicts an example of a shape model.

FIG. 3 depicts an illustration of the average shape 300 of an organ (here a liver) with anatomical landmarks labels 320 applied to indices corresponding to these anatomical points. The illustration also depicts an example of such a labeling applied to entire structures such as the ligaments of the liver. In the figure, indices of the average shape corresponding to key points or landmarks 320 are shown with a cross 'x' or a plus '+'. The highlighted area may represent the path 310 of a sweep. Different paths may be predefined and may be configured to cover specific landmarks on the organ. Alternatively, the path may be performed without instruction.

At act A120, a trajectory of an ultrasound probe is tracked over the one or more landmarks 320 during a procedure to acquire the ultrasound image data. Medical ultrasound probes may be used to generate cross sectional ultrasound images of a patient. The probe may be moved over a body of a patient while transmitting. The probe transmits signals including short bursts of ultrasonic energy. After each burst, the probe waits for a return signal within a small window of time corresponding to the time for the energy to reflect from parts of the object. Upon receiving the echo, the probe turns the sound waves into electrical energy that may be measured and used to generate ultrasound image data.

Varied sizes or shapes of transducers may be used for different ultrasound procedures. For example, the shape of the probe determines a field of view. Ultrasound transducers for cardiac scans may the smallest; vascular ranges in size from 25 mm to 50 mm; abdominal/curved shape has a larger footprint, and transvaginal transducers are long and skinny with a small head. The shape of the head may affect the type of scan. For example, for a sector, linear, or curved scan, the shape may be different.

Figure 4:
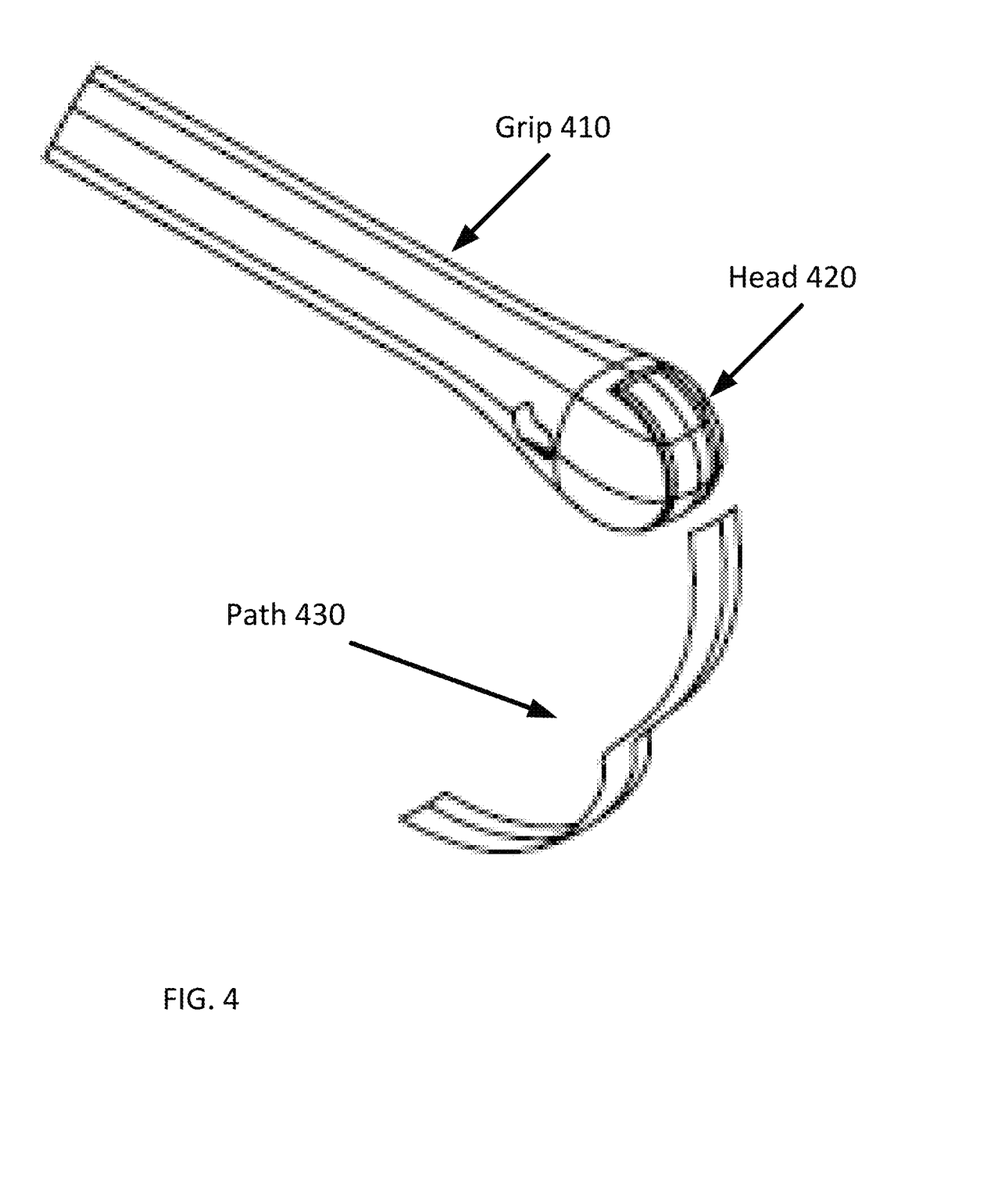
FIG. 4 depicts an example of an ultrasound transducer.

FIG. 4 depicts a distal end (scan head) of an example handheld ultrasound transducer. The transducer includes a neck 410 and a head 420. The path 430 that the head 420 takes when passed over an object is also depicted. The path 430 may be generated as a function of the shape of the head 420, the shape of the object, the pressure asserted by a user, and the properties of the object (compression, elasticity, etc.). Robotically operated transducers may be used in other embodiments.

During an ultrasound procedure, the transducer moves (e.g., due to the user or robot) over a surface of the patient body. In order to acquire an accurate image, the transducer may be pressed against the body to eliminate any gaps of air or other substance that may affect the scan. In the process of pressing the transducer against a patient's body, the patient's tissue may be deformed where the transducer is located, for example, conforming to the shape of the head 420 of the transducer. During the procedure, the head 420 of the transducer is tracked. The tracked trajectory is stored along with the corresponding ultrasound image data. Tracking the head 420 of the transducer may be accomplished by using different techniques, such as correlation of the ultrasound data resulting from the scan and/or magnetic position sensors on the transducer.

FIG. 4 depicts the path 430 of the trajectory of an outer surface (e.g., acoustic window) of the head of the ultrasound probe. The rest or all of the transducer moves in a same or different path. As tracked, the path 430 may represent a three-dimensional mesh of the transducer head 420 as the head 420 passes over the body of a patient. The three-dimensional mesh is extruded along the sweep to result in the path 430 as illustrated in FIG. 4. The mesh points may correspond to the points in the shape model as depicted by the sweep path 310 in FIG. 3.

An ultrasound system may include a tracking system for tracking the movement of the transducer. Different tracking systems may be used. In an embodiment, the probe contains a tracking device that obtains the positional information of the probe, the patient, and/or operator to a fixed point. The sweep of the probe is derived from the positional information. The tracking system may include combinations of infrared (IR) depth sensors, optical cameras, accelerometers, and/or gyroscopes for identifying and locating any combination of a probe, an operator, and a patient in a predetermined space. In an embodiment, the combination of an accelerometer and a gyroscope is mounted on a probe to track an amount of change in movement, angle, and/or direction. Other exemplary sensors, such as an IR depth sensor and an optical camera, are optionally used to track an amount of movement. The tracking system may include one or more different tracking models for different models of transducers. For example, different heads on the transducers may be tracked differently.

The transducer may be tracked automatically. For example, a probe positioning system is a tool for the automated positioning of a (hand-held) measuring device, such as an ultrasound transducer in a fixed, predetermined place to the object, such as a patient.

In an embodiment, the tracking system may require determining an initial point of reference. For example, a transducer in contact with the skin of a patient without pressure may be used as a reference point to calibrate the sweep of an ultrasound procedure. A user may perform a reference sweep over the body of a patient without any pressure.

The tracked trajectory and ultrasound image data may be stored in a memory, for example a PACS. The tracked trajectory may be used to register the ultrasound images to preoperative images. The registered images may be displayed to a user during or after the ultrasound procedure.

At act A130, the geometry is deformed as a function of the tracked trajectory. The transducer is tracked in act A120 over a portion of a patient's body that includes one or more of the landmarks. The path 430 of the tracked trajectory may then be imputed to the geometry of the segmented preoperative image. In an embodiment, the tracked trajectory may be imputed to a shape model used in act A110. Each of the landmark points that were swept are adjusted based on the tracked trajectory. The segmented preoperative image may be adjusted as the landmark points are deformed.

In an embodiment, an initial rigid alignment between the geometry and the path of the ultrasound sweep may be obtained using: $\text{minimize} \|ps - P \cdot T \cdot pu\|$ (1) where ps and pu are the points of the geometry and ultrasound sweep, respectively. P and T are permutation and transformation matrices, respectively. The minimization equation may be solved, for example, using CPD or ICP. The initial rigid alignment may identify the deformation between the geometry and the ultrasound sweep. The deformation may be used to generate a deformed geometry, e.g. deformed segmented preoperative image data, that includes the tissue deformation caused by the sweep of the transducer.

In an embodiment, the sweep may not cover the organ from each side. As a result, the alignment and deformation may be coarse. Multiple sweeps may be used and tracked to refine the alignment. A combined three-dimensional volume may be generated from the acquired ultrasound images. Key points are then identified in this volume.

Referring back to FIG. 3, key landmark points 320 may be identified from the geometry to constrain the solution of the minimization equation described above. Once the landmark points 320 are defined, the geometry is deformed using a Thin Plate Spline method. Thin plate spline methods may be used to estimate the deformation between two images. Thin Plate Splines are used to produce approximations to given data in more than one dimension. A Thin plate spline is produced by solving for $\text{minimize} \|D \cdot ps\| + \Sigma \|\overline{pl,i} - \overline{pu,i}\| N$ i=1 (2) Where D is the deformation of the geometry, $\overline{pl,i}$ and $\overline{pu,i}$, are the centroids of the labeled points in average shape and identified key points in the tracked trajectory, respectively. The equation may minimize the error when calculating the deformation between the key points as identified by the geometry and the points identified in the tracked trajectory.

At act A140, the deformed geometry (e.g. deformed segmented preoperative image data) is registered with the ultrasound image data. Points between the deformed segmented preoperative image data may be matched with points in the ultrasound image data. The alignment between the two sets of points may be determined using any point matching technique. For example, ICP or CPD may be used. ICP performs rigid registration in an iterative fashion by assuming that every point in the preoperative image data corresponds with the closest point to a point in the ultrasound image data and then finding the least squares rigid transformation. CPD provides a probabilistic method for non-rigid registration of two point sets. The registration is considered as a maximum likelihood estimation problem, where one point set represents centroids of a Gaussian mixture model and the other represents the data.

The ultrasound image data may be segmented prior to being aligned with the deformed preoperative image segmentation data. Segmentation of the ultrasound image data may be accomplished using the deformed geometry or shape model.

In an embodiment, there may exist four different sets of points. A set of points in a preoperative image data of the organ. A set of points in a shape model of the organ. A set of points in the sweep trajectory and a set of points in an ultrasound image data. Each of the set of points may correspond to anatomical landmarks. The points may be registered with one another in order to generate a display of image data from both the preoperative images and ultrasound images. As described above, the set of points in the preoperative images are matched to the shape model through segmentation. The points in the sweep are matched to the segmented set of points to generate a deformed set of points. The deformed set of points may be matched to the points in the ultrasound image data. Alternative matching schemes may be used. For example, the set of points in the sweep may be used to match the ultrasound sweep to the shape model. The shape model may then be used to match the ultrasound image data points with the preoperative segmented points.

At act A150, after registration, the preoperative images and ultrasound images may be displayed. In an embodiment, the preoperative images are deformed to match the ultrasound images. Alternatively, the ultrasound images may be deformed to match the preoperative images. For example, the deformation caused by the ultrasound probe may be visible (if the preoperative images are deformed to include the deformation) or may not be visible (if the ultrasound images are deformed to match the non-deformed preoperative images). The images are displayed next to each other from a same perspective. Alternatively, or additionally, one image is overlaid with another. In yet other embodiments, information derived from one set of data (e.g., landmark near the transducer head) is displayed in an image from the other set of data (e.g., preoperative image data) using the spatial transform. An image of the shape model and/or transducer model may be displayed, such as a mesh overlay with an ultrasound, preoperative, or fusion of ultrasound and preoperative image.

The registered images may be displayed with additional information or preferences. The registered images may be stored, for example, in a PACS for later use. The preoperative images, ultrasound images, and/or deformation information may be used to register additional image data or volumes from prior or future scans.

The points in the shape model or segmented preoperative image data were deformed in act A130 to match the path of the ultrasound probe. In an alternative embodiment, the deformation of the shape model or segmented preoperative images is calculated using a biomechanical model.

Figure 5:
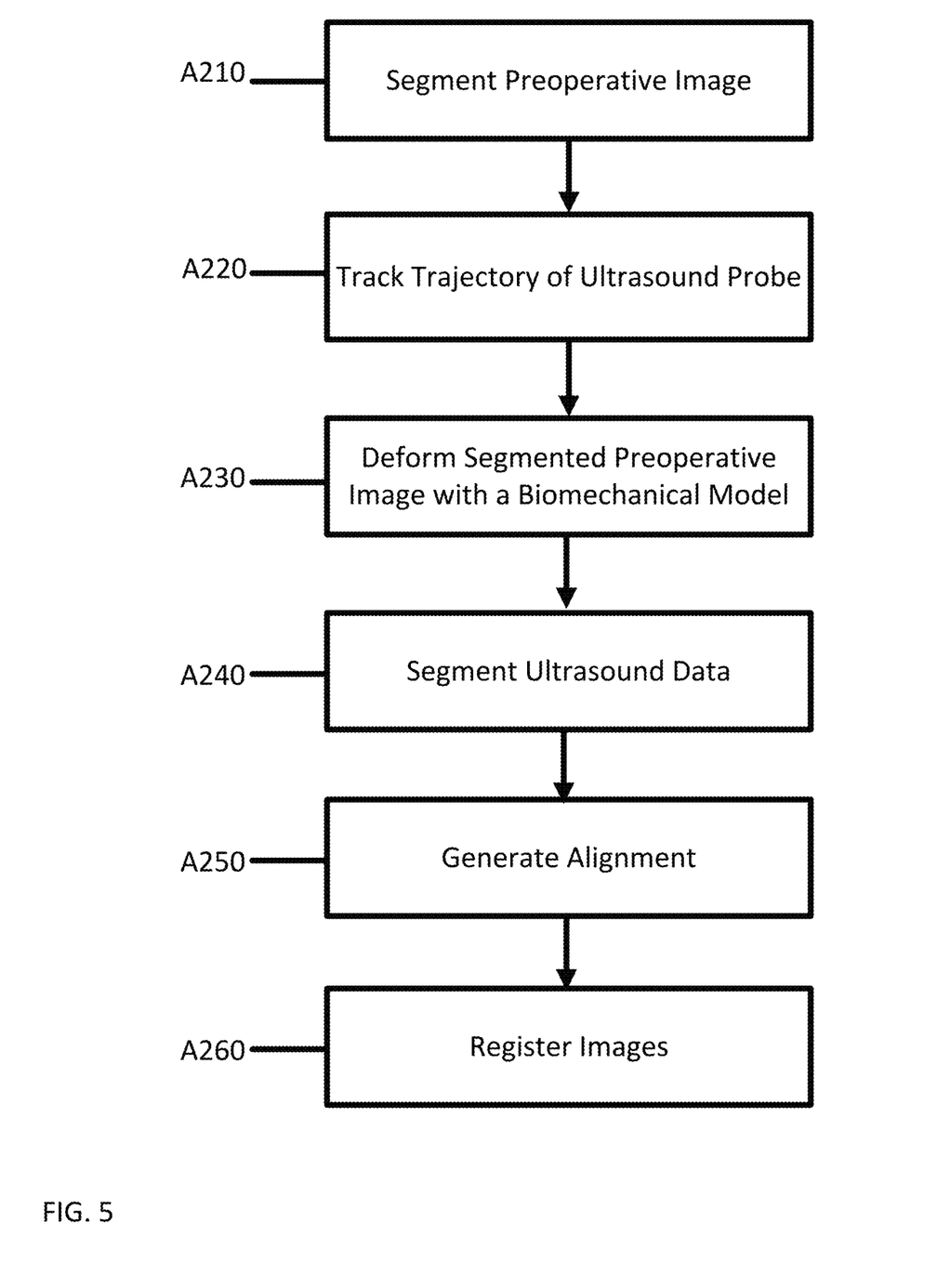
FIG. 5 depicts a flow chart of another embodiment of a method for registration of intra-operative ultrasound images to preoperative images.

FIG. 5 depicts a diagram of one embodiment of a method for registering preoperative images with ultrasound images using a biomechanical model. The method relates to tracking a deformation due to an ultrasound procedure and using the deformation and the biomechanical model to register ultrasound image data with previously captured image data. The biomechanical model of organ deformation is used to deform a shape model using a trajectory of the transducer as boundary condition. The deformed shape model is used to segment the organ in a reconstructed three-dimensional ultrasound volume from the sweep. The segmented organ from the reconstructed 3D volume is registered to the segmented volume from the preoperative modality.

The medical system of FIG. 6 or other medical system implements the acts. The system may be a medical imaging system, a hospital workstation, a medical server, or other secure medical data processing system. The medical system may or may not include a memory or database, such as patient medical record database and/or picture archiving and communications system (PACS). The system includes an ultrasound system including an ultrasound transducer (probe). The ultrasound system may include the medical imaging system or the medical imaging system may include the ultrasound system.

The acts of FIG. 5 are performed in the order shown (numerical or top to bottom) or other orders. For example, acts A240 and A250 occur simultaneously or in any order. Additional, different, or fewer acts may be provided. Example additional acts include acquiring the preoperative image or displaying the images.

At act A210, a preoperative volume is segmented. The preoperative volume may be acquired using any imaging technique. Similar to Act A110, the preoperative image may represent an internal structure in a patient. In the examples below, medical imaging or scanner data is used. In other embodiments, other types of data are used. A medical scanner may provide the image data, such as a medical dataset representing a 2D slice or 3D region of the patient. Any type of image data may be obtained, such as computed tomography, magnetic resonance, positron emission tomography, single photon emission computed tomography, ultrasound, or another scan modality. The scan data may represent one or more objects, for example, the internal organs of a patient.

The preoperative volume may be segmented using a shape model technique. A shape model may use a standard statistical model of an object. A set of landmarks are selected that describe the shape of the object that may be found reliably on training images. To collect information about the shape variations needed to build the model, a set of landmark points or landmarks represents each shape. The number of landmarks may be adequate to show the overall shape and also show details. Each shape may be represented by a predefined number of landmarks, this number depends on the complexity of the object's shape and a level of detail description. Landmarks may be, for example, points at clear corners of object boundaries, 'T' junctions between boundaries or easily located biological landmarks. The model may be generated from the set of landmarks. Given a rough starting approximation, an instance of the model may be fit to the preoperative image using fitting techniques such as ICP or CPD.

At act A220, a path of an ultrasound transducer is tracked during an ultrasound procedure to acquire ultrasound image data. The ultrasound transducer may be pressed against the skin or surface of a patient or object. The ultrasound transducer is then swept across the surface to acquire an ultrasound volume. Pressure is applied to the ultrasound transducer to provide constant contact. As a result of the pressure, the tissue of a patient or an object may be deformed. The deformation may be directly related to the path of the transducer. The path may be tracked using a tracking system. Different tracking systems may be used. In an embodiment, the probe contains a tracking device that obtains the positional information of the probe, the patient, and/or operator to a fixed point. The sweep of the probe is derived from the positional information. The tracking system may include combinations of infrared (IR) depth sensors, optical cameras, accelerometers, and gyroscopes for identifying and locating any combination of a probe, an operator, and a patient in a predetermined space.

The tracking system may generate a three-dimensional geometry of the ultrasound sweep. In an embodiment, the sweep is performed over one or more anatomical landmarks. The three-dimensional geometry may match up with the one or more anatomical landmarks. For example, a sweep may be performed to cover a specific portion of an organ that contains one or more landmarks.

At act A230, a deformation of the segmented preoperative volume is calculated using a biomechanical model and the path of the ultrasound transducer. The biomechanical model may use the path as a boundary condition for calculating the deformation. The biomechanical model may be based on tissue compression of the organ. For example, for an organ tissue that has a compression ratio of 10%, when pressed 1.0 centimeters, the tissue may deform by 0.1 centimeters. Compression and other properties of tissues may vary and may be determined and stored for use in the model. The effect of the pressure of the transducer may cause different tissues or different regions to deform differently. The biomechanical model of an organ may take the organ shape and size into consideration. An organ that is circular may spread the deformation over the entire structure. A nonsymmetrical organ, such as the liver, may deform differently over different portions. A portion of the organ closest to the ultrasound transducer may deform more than a portion of the organ that is further away.

The deformation of an organ may be modeled by the biomechanical model so that surrounding tissues and objects are taken into consideration. An organ may suffer more deformation if the surrounding material is compressible. An organ surrounded by a hard material or uncompressible material may not deform as much. For example, an organ or object located near a bone may not deform as much as an organ surrounded by soft tissue. An organ filled with a first material may deform less than an organ filled with a second material. For example, the contents of a stomach or lumen in the patient's body may be taken into consideration. Older tissue may deform less than newer tissue.

The biomechanical model may be generated individually for patients. Alternatively, the biomechanical model may be generated and stored globally for distinct types of organs or tissues. For example, a different biomechanical model may be used for a heart volume, a stomach volume, a pancreas volume, a kidney volume, etc. The biomechanical model may be based on a finite element method (FEM) solution. Finite element modelling is a computational technique that may be used to solve biomedical engineering problems based on the theories of continuum mechanic. Continuum mechanics deals with the analysis of the kinematics and the mechanical behavior of materials modeled as a continuous mass rather than as discrete particles. FEM uses three major stages to analyze tissues: pre-processor, solution, and the post process stage. In the pre-process stage, a structural model is generated. The geometry and material properties the tissues may be acquired from, for example, computed tomography (CT). Once the model is developed the mesh generation is carried out. The material properties to each model is assigned and finally boundary conditions are applied.

In an embodiment, a FEM method is used for the equations of motion describing the modes of deformation in the biomechanical model. Using FEM, the method discretizes the domain as a tetrahedral mesh from the geometry of the segmented preoperative volume surface. The tissue displacement field at static equilibrium is solved using a 3D Navier-Cauchy equation:

$$\frac{E}{2(1+v)(1-2v)}\nabla(\nabla \cdot u) + \frac{E}{2(1+v)}\nabla^2 u + F = 0 \quad \text{EQUATION 1}$$

where E is Young's modulus, v is Poisson's ratio, u is the 3D displacement vector at a point in the tissue, and F is the applied body force distribution. The displacement is determined using the equation for each point of the tissue.

In an embodiment, linear basis functions may be used that are defined on the tetrahedral elements. A Galerkin weighted residual method is used to construct a linear system of equations with the form: Ku=f, where K is the stiffness matrix containing contributions from the material properties and constitutive equation, u is the vector of mesh nodal displacements, and f contains a vector of applied boundary conditions. The displacement conditions are calculated for the boundary nodes in f based on the vectors mapping from the segmented preoperative volume to the tracked trajectory. The displacement boundary conditions identified from the segmentation correspondences are assigned by modifying the appropriate equation to give a final system of equations: Au=b that is solved for the nodal displacements that satisfy the boundary conditions and material properties.

At act A240, the ultrasound data is segmented using the deformed segmented preoperative volume as an initial shape representation. A shape model method may be used with the deformed segmented preoperative volume used as the average shape. After deforming the pre-op mesh model of the organ with the boundary condition arising from the transducer interaction, the deformed model may be used as initial shape representation for segmentation of the ultrasound image data. Additional key landmark points derived from prior images or by picking a few points on the screen may be used to augment the organ segmentation.

At act A250, a non-rigid alignment is determined between the segmented ultrasound data and segmented preoperative volume. Using the alignment, the preoperative image may be superimposed on the intra-operative ultrasound images to result in full image registration. The preoperative volume and ultrasound volume may be rendered together into an image for display. The image may be rendered in real time as the ultrasound procedure is performed. Alternatively, if the ultrasound procedure is performed before the preoperative images are acquired, the image may be rendered as the preoperative images are acquired. At act A260, the ultrasound data and preoperative volume may be registered and displayed.

FIG. 6 depicts a system for registration of a preoperative volume and an ultrasound image. The system includes a medical imaging system 540, an ultrasound system 520, a memory 510, a processor 530, and a display 550. The ultrasound system 520 includes an ultrasound transducer and a tracking system.

The medical imaging system 540 may include be a CT scanner, MR scanner, or other imaging system. Alternatively, the medical imaging system 540 is a workstation, computer, or server for using data acquired by a separate system in real-time or using previously acquired patient-specific data stored in a memory. For example, a separate database, server, workstation, imaging system, and/or computer may be provided for acquiring and storing preoperative images. The ultrasound system 520 is provided for acquiring ultrasound data representing a volume. The ultrasound system includes a tracking system to track the transducer during an ultrasound procedure. Additional, different, or fewer components may be used.

The ultrasound system 520 includes a transmit beamformer, receive beamformer, B-mode detector, Doppler detector, harmonic response detector, contrast agent detector, scan converter, filter, combinations thereof, or other now known or later developed medical diagnostic ultrasound system components.

The ultrasound system 520 is configured to scan a volume of a patient. The operator selects an imaging application and/or adjusts various settings to provide the desired frame rate, field of view, mode of imaging, and/or image rendering. In response, the ultrasound system 520 provides medical diagnostic ultrasound data representing at least a part of the patient's anatomical structure over time. A sequence of frames of data representing a volume of the patient over time is acquired. The ultrasound system 520 includes a transducer that may be operated by an operator.

The transducer 522 may be a piezoelectric or capacitive device operable to convert between acoustic and electrical energy. The transducer 522 is an array of elements, such as a multi-dimensional or two-dimensional array. Alternatively, the transducer 522 is a wobbler for mechanical scanning in one dimension and electrical scanning in another dimension. In another embodiment, the array is a one-dimensional array on a cardiac catheter or a TEE probe. Multi-dimensional arrays or a plurality of one-dimensional arrays may be provided on a TEE probe.

The ultrasound system 520 uses the transducer 522 to scan a volume of a patient. Electrical and/or mechanical steering allows transmission and reception along different scan lines in the volume. Predefined scan patterns may be used. For example, a plurality of different sweeps across the surface of a patient that cover anatomical landmarks may be defined.

The scan provides the medical diagnostic ultrasound data representing the organ or internal structure at separate times as a sequence. The scan may be repeated to provide data for the volume at separate times. Ultrasound data representing a volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data may be of any type, such as B-mode, flow mode (e.g., PW Doppler), spectral mode (e.g., CW Doppler), Doppler mode, contrast agent, harmonic, or other ultrasound modes of imaging.

The tracking system 524 may include infrared (IR) depth sensors, optical cameras, accelerometers, magnetic coils, gyroscopes, or combinations thereof for identifying and locating any combination of the transducer (or probe), an operator and a patient in a predetermined space. The tracking system 524 may record the position and alignment of the transducer or probe as the scan is performed. The tracking system 524 may be configured to generate a 2D or 3D model of the deformation caused by the transducer 522 or ultrasound probe against a patient's body.

The processor 530 is a general processor, digital signal processor, three-dimensional data processor, graphics processing unit, application specific integrated circuit, field programmable gate array, digital circuit, analog circuit, combinations thereof, or other now known or later developed device for registering two or more images. The processor 530 is a single device, a plurality of devices, or a network. For more than one device, parallel or sequential division of processing may be used. Different devices making up the processor 530 may perform distinct functions, such as an image segmentation or image registration and a separate graphics processing unit for rendering images of the anatomy. In one embodiment, the processor 530 is a control processor or other processor of a medical diagnostic imaging system, such as a medical diagnostic ultrasound imaging system processor. The processor 530 is configured by or operates pursuant to stored instructions to perform various acts described herein, such as any or all of the acts in FIGS. 2 and 5.

In one embodiment, the processor 530 is configured by software, firmware, and/or hardware to register preoperative images with ultrasound image data using image segmentation, a shape model, and a trajectory of a probe used to acquire the ultrasound image data.

In an additional or alternative embodiment, the processor 530 may be configured to identify a biomechanical model for an object. The processor 530 may calculate the deformation of the object based on the biomechanical model and a tracked sweep of a transducer 522 during an ultrasound procedure. The deformation may be used to register preoperative images acquired by the medical imaging system 540 and intraoperative images from the ultrasound procedure.

The processor 530 may be configured to render a view including image data from either the preoperative image, ultrasound image, or both. The processor 530 may be configured to deform or alter the preoperative image, ultrasound image, or both in order to overlay the images together. The deformation may be calculated as a function of the registration of the images.

The display 550 is a CRT, LCD, plasma, projector, printer, or other output device for showing an image. The display 550 displays a view of the preoperative images, ultrasound images, or both. Additional images or medical data may be overlaid or highlighted based on user preferences.

The memory 510 is a buffer, cache, RAM, removable media, hard drive, magnetic, optical, database, or other now known or later developed memory. The memory 510 is a single device or group of two or more devices. The memory 510 is shown connected with the processor 530, but may be outside or remote from other components of the processor 530.

The memory 510 stores the preoperative image data, ultrasound image data, transducer trajectory data, shape model data, segmented image data, and registration data (e.g., transformation). Alternatively, the data is transferred to the processor 530 from another device. The image data may be a three-dimensional data set, or a sequence of such sets. The data represents a three-dimensional region. Any format may be used, such as voxels interpolated to a three-dimensional grid or data representing parallel or non-parallel planes.

The memory 510 is additionally or alternatively a non-transitory computer readable storage medium with processing instructions. The memory 510 stores data representing instructions executable by the programmed processor 530 for registering images. The instructions for implementing the processes, methods and/or techniques discussed herein are provided on computer-readable storage media or memories, such as a cache, buffer, RAM, removable media, hard drive, or other computer readable storage media. Computer readable storage media include diverse types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code, and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for registration of a preoperative volume and ultrasound data, the method comprising:
generating a segmented preoperative volume of an organ from the preoperative volume, the segmented preoperative volume comprising at least one or more anatomical landmarks;
tracking a path of an ultrasound transducer over the one or more anatomical landmarks during a procedure to acquire the ultrasound data;
generating a three-dimensional mesh of the path of the ultrasound transducer during the procedure;
computing an initial rigid alignment between the segmented preoperative volume and the three-dimensional mesh;

determining a deformation between the segmented preoperative volume and the three-dimensional mesh using at least the initial rigid alignment;

adjusting, based on the determined deformation, one or more positions of the one or more of the anatomical landmarks in the segmented preoperative volume;

generating a deformed segmented preoperative volume including the adjusted one or more anatomical landmarks; and registering the deformed preoperative volume to the ultrasound data.

2. The method of claim 1, wherein generating the segmented preoperative volume comprises:

segmenting the preoperative volume with a shape model.

3. The method of claim 2, wherein the shape model comprises an average shape of the organ.

4. The method of claim 3, wherein the segmented preoperative volume comprises one or more modes of variation of the organ and one or more coefficients for the one or more modes of variation.

5. The method of claim 1, wherein the one or more anatomical landmarks comprise correspondence points for registering the deformed segmented preoperative volume to the ultrasound data.

6. The method of claim 1, wherein tracking the path comprises tracking the ultrasound transducer with a motion sensor.

7. The method of claim 1, wherein tracking the path comprises tracking the ultrasound transducer with an infrared sensor.

8. The method of claim 1, wherein determining the deformation is based on the initial rigid alignment using a spline-based technique.

9. The method of claim 1, wherein further comprising:

segmenting, prior to registering, the ultrasound data using the deformed segmented preoperative volume; and registering the deformed segmented preoperative volume to the segmented ultrasound data.

10. The method of claim 1, further comprising:

displaying the deformed preoperative volume overlaid with the ultrasound data.

11. A system for registration of a preoperative volume and an ultrasound volume, the system comprising:

a medical imaging system configured to acquire the preoperative volume;

an ultrasound transducer configured to acquire the ultrasound volume;

a tracker configured to track a path of the ultrasound transducer over one or more anatomical landmarks; and a processor configured to generate a segmented preoperative volume of the preoperative volume comprising the one or more anatomical landmarks, the processor further configured to generate a three-dimensional mesh of the path of the ultrasound transducer, compute an initial alignment between the three-dimensional mesh and the segmented preoperative volume, and adjust based on the initial alignment and one or more identified key points, one or more positions of the one or more of the anatomical landmarks in the segmented preoperative volume, the adjustment reflective of tissue deformation caused by the path of the ultrasound transducer, generate a deformed preoperative volume including the adjusted one or more anatomical landmarks, and register the deformed preoperative volume to the ultrasound volume.

12. The system of claim 11, further comprising:

a display configured to simultaneously display a combined view of the preoperative volume and ultrasound volume.

13. The system of claim 11, wherein the processor generates the segmented preoperative volume using an average shape model.

14. The system of claim 11, wherein the tracker comprises an infrared depth sensor.

\* \* \* \* \*